United States Patent

Kimoto et al.

[11] Patent Number: 4,536,352
[45] Date of Patent: Aug. 20, 1985

[54] PERFLUORO VINYL ETHERS

[75] Inventors: Kyoji Kimoto, Kanagawa; Hirotsugu Miyauchi, Tokyo; Jukichi Ohmura, Kanagawa; Mikio Ebisawa, Kanagawa; Toshioki Hane, Kanagawa, all of Japan

[73] Assignee: Asahi Kasei Kogyo Kabushiki Kaisha, Osaka, Japan

[21] Appl. No.: 330,608

[22] Filed: Dec. 14, 1981

Related U.S. Application Data

[62] Division of Ser. No. 152,856, May 23, 1980, U.S. Pat. No. 4,329,435.

[30] Foreign Application Priority Data

| May 31, 1979 | [JP] | Japan | 54-67889 |
| Jul. 18, 1979 | [JP] | Japan | 54-90302 |
| Dec. 21, 1979 | [JP] | Japan | 54-165675 |
| Dec. 26, 1979 | [JP] | Japan | 54-168179 |
| Dec. 28, 1979 | [JP] | Japan | 54-170315 |

[51] Int. Cl.³ .......................................... C07C 143/70
[52] U.S. Cl. .................................................. 260/543 F
[58] Field of Search ..................................... 260/543 F

[56] References Cited

U.S. PATENT DOCUMENTS

| 4,151,653 | 4/1979 | Seko et al. | 204/98 |
| 4,176,215 | 11/1979 | Molnar et al. | 521/27 |
| 4,275,226 | 6/1981 | Yamabe et al. | 260/543 F |
| 4,348,310 | 9/1982 | Silva et al. | 260/543 F |

FOREIGN PATENT DOCUMENTS

| 126398 | 11/1976 | Japan . |
| 23192 | 2/1977 | Japan . |
| 28588 | 3/1977 | Japan . |
| 36589 | 3/1977 | Japan . |
| 104583 | 9/1978 | Japan . |
| 116287 | 10/1978 | Japan . |
| 132089 | 11/1978 | Japan . |
| 6887 | 1/1979 | Japan . |
| 1497748 | 1/1978 | United Kingdom . |

*Primary Examiner*—Natalie Trousof
*Assistant Examiner*—L. Hendriksen
*Attorney, Agent, or Firm*—Birch, Stewart, Kolasch & Birch

[57] ABSTRACT

A novel fluorinated copolymer is prepared by copolymerization of a fluorinated olefin with a novel sulfur containing fluorinated vinylether of the formula:

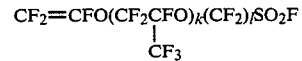

$$CF_2=CFO(CF_2CFO)_k(CF_2)_lSO_2F$$
$$|$$
$$CF_3$$

wherein k is 0 or 1 and l is an integer of 3 to 5, which is prepared from starting materials which are also novel. Said copolymer is useful for preparation of a fluorinated cation exchange membrane having carboxylic acid groups and/or sulfonic acid groups which can be used advantageously in electrolysis of an aqueous alkali metal halide solution with improved electrolysis performance.

2 Claims, No Drawings

PERFLUORO VINYL ETHERS

This application is a divisional of copending application Ser. No. 152,856, filed on May 23, 1980, Pat. No. 4,329,435.

This invention relates to a novel fluorinated copolymer useful as a starting material for production of a fluorinated cation exchange membrane or a fluorinated cation exchange resin having sulfonic acid groups and/or carboxylic acid groups and also to a process for preparing the same.

In recent years, there has been an increasing trend for development of new chemical processes using fluorinated cation exchange membranes or resins excellent in chemical resistance and heat resistance. As a typical example of such a trend, the ion-exchange membrane process has recently attracted great attention in the chloro-alkali industry wherein caustic soda and chlorine are produced by electrolysis of sodium chloride, because it is more advantageous in various aspects such as prevention of environmental pollution and economical saving of energy than the mercury process and the diaphragm process of the prior art and also because it can produce caustic soda having substantially the same quality as that produced by the mercury process.

The greatest factor which controls the economy of the ion-exchange membrane process is the characteristic of the cation exchange membrane employed. It is necessary for the cation exchange membrane to satisfy the requirements as set forth below. (1) To have a high current efficiency and a low electric resistance. In order to have a high current efficiency, the membrane is required to have a sufficiently high ion-exchange capacity and low water content, thus giving a high concentration of fixed ions in the membrane. On the other hand, to the effect of lower electric resistance, a higher water content is rather more advantageous. Since the water content will vary depending on the types of ion-exchange groups, the ion-exchange capacity and the concentration of external solutions, it is necessary to select the optimum combination of these factors.

(2) To be resistant to chlorine and alkali at higher temperatures for a long time. A cation exchange membrane comprising a fluorinated polymer can be sufficiently resistant generally under the aforesaid atmosphere, but some membranes may be insufficient in chemical stability depending on the ion-exchange groups contained therein. Accordingly, it is important to select suitable ion-exchange groups.

(3) To be durable for a long time under various stresses working in highly concentrated alkali under the conditions of high temperature and high current density such as a stress of swelling and shrinking, a stress accompanied by vigorous migration of substances to effect peel-off of layers and a stress by vibration of the membrane accompanied with gas generation to cause bending cracks. Generally speaking, the physical strength of the membrane is different depending on the physical structure of the membrane, the polymeric composition, the ion-exchange capacity and the types of ion-exchange groups. Therefore, it is necessary to realize the optimum selection of these factors.

(4) To be easily produced and low in cost.

In the prior art, there have been proposed several fluorinated cation exchange membranes for use in electrolysis of an aqueous alkali metal halide solution. For example, there is known a fluorinated cation exchange membrane having pendant sulfonic acid groups prepared by hydrolysis of a copolymer comprising tetrafluoroethylene and perfluoro-3,6-dioxa-4-methyl-7-octene sulfonylfluoride.

Such a well-known fluorinated cation exchange membrane containing only sulfonic acid groups, however, is liable to permit permeation of hydroxyl ions migrated and diffused from the cathode compartment therethrough due to the high water content afforded by the sulfonic acid groups. For this reason, such a membrane is disadvantageously low in current efficiency. In particular, when electrolysis is conducted, for example, by recovering a highly concentrated caustic soda solution of 20% or higher, the current efficiency is extremely low to a great economical disadvantage as compared with electrolysis by the mercury process or the diaphragm process of the prior art.

For improvement of such a drawback of low current efficiency, the ion-exchange capacity of sulfonic acid groups may be lowered to, for example, 0.7 milliequivalent or lower per one gram of the H-form dry resin, whereby the water content in the membrane can be decreased to make the fixed ion concentration in the membrane higher than the membrane with higher ion-exchange capacity. As the result, the current efficiency at the time of electrolysis can slightly be prevented from being lowered. For example, when electrolysis of sodium chloride is performed while recovering caustic soda of 20% concentration, the current efficiency can be improved to about 80%. However, improvement of current efficiency by reduction in ion-exchange capacity of the membrane will cause a noticeable increase in the electric resistance of the membrane, whereby no economical electrolysis is possible. Moreover, at any higher value of the electric resistance of the membrane, it is very difficult to prepare a commercially applicable sulfonic acid type fluorinated cation exchange membrane improved in current efficiency to about 90%.

On the other hand, Japanese published unexamined patent applications No. 120492/1975 and No. 126398/1976 disclose fluorinated cation exchange membranes having carboxylic acid groups as ion-exchange groups. In these membranes, the fixed ion concentration can be made higher due to the lower water content of carboxylic acid groups and therefore the current efficiency can be improved to 90% or higher. Such membranes are also chemically stable under the conditions conventionally used.

When compared at the same level of the ion-exchange capacity, however, the membrane having carboxylic acid groups is higher in electric resistance than the membrane having sulfonic acid groups. Particularly, when used at a high current density, the power unit may be undesirably very high. Moreover, perhaps due to lower water content throughout the membrane, the membrane is prone to shrink when used for a long time in a highly concentrated alkali under severe conditions until it is hardened so as to be brittle, resulting in layer peel-off or crack formation, whereby current efficiency may disadvantageously be lowered.

For improvement of such drawbacks of the membrane having only carboxylic acid groups, there is also known a cation exchange membrane prepared by bonding films of a fluorinated polymer having carboxylic acid groups or groups convertible to carboxylic acid groups (hereinafter referred to as precursors) and a fluorinated polymer having sulfonic acid groups or precursors thereof or by molding a blend of said polymers into a film, followed by hydrolysis, as disclosed by Japanese published unexamined patent applications No. 36589/1977 and No. 132089/1978, and U.S. Pat. No. 4,176,215. However, these polymers are poorly compatible and it is difficult to effect complete bonding or blending. When used under severe conditions, such a membrane is liable to suffer from peel-off or formation of cracks and thereby to cause troubles. The blended product is also entirely insufficient from the standpoint of complete utilization of higher current efficiency of carboxylic acid groups and lower electric resistance of sulfonic acid groups. It merely exhibits the intermediate characteristic of both properties.

The aforesaid Japanese published unexamined patent applications and another Japanese published unexamined patent application No. 23192/1977 also disclose a cation exchange membrane prepared by ternary copolymerization of a vinyl monomer having carboxylic acid groups or precursors thereof, a vinyl monomer having sulfonic acid groups or precursors thereof and a fluorinated olefin, followed by fabrication into a film and hydrolysis. Such a membrane also merely shows the intermediate characteristic.

On the other hand, there are disclosed cation exchange membranes prepared by forming carboxylic acid groups by chemical treatment on one surface of fluorinated cation exchange membranes having sulfonic acid groups, as disclosed by Japanese published unexamined patent applications No. 24176/1977, No. 104583/1978, No. 116287/1978 and No. 6887/1979. These membranes, due to the presence of carboxylic acid groups, will effectively inhibit migration and diffusion of hydroxyl ions to exhibit higher current efficiency. Also, since the carboxylic acid groups are present in the thin layer on the cathode side and sulfonic acid groups with higher water content in the residual part of the membrane, the electric resistance of the membrane is low. Thus, these membranes are very excellent from the standpoint of the power unit. However, all of these membranes, while they are stably used with good performance under conventional conditions for a commercially satisfactory term, will suffer, under severe conditions of further increased high current density and high temperature, from swelling like splotch or formation of water bubbles, peel-off of the carboxylic acid layer from the sulfonic acid layer or formation of cracks in the carboxylic acid layer, thereby causing a decrease in current efficiency.

It has not yet been clarified why such phenomena are caused. Presumably, the polymeric structure of the fluorinated cation exchange membrane having sulfonic acid groups or derivatives thereof may be one of the factors for such phenomena. That is, these membranes are prepared by chemical treatment of a copolymer of a fluorinated olefin with a sulfur containing fluorinated vinylether as represented by the following formula formed in the shape of a membrane or a hydrolyzed product thereof having sulfonic acid groups:

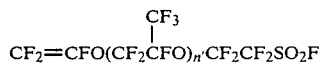

$$CF_2=CFO(CF_2CFO)_{n'}CF_2CF_2SO_2F$$
$$\quad\quad\quad\quad\;\;\; |$$
$$\quad\quad\quad\quad CF_3$$

wherein n' is an integer of 0 to 2.

Among said monomers, the monomer of n'=0 will cause the cyclization reaction as shown by the reaction scheme (1) below in the vinylization step as disclosed by Japanese published examined patent application No. 2083/1972.

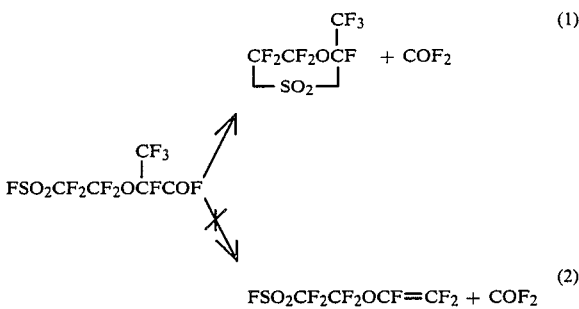

For converting the cyclic sulfone to $CF_2=CFOCF_2CF_2SO_2F$, a number of reaction steps are required to be performed and therefore it is very difficult to produce said monomer in commercial application. Moreover, depending on the conditions, such cyclization will also occur at the time of polymerization and may lower the properties of the resultant polymer.

For this reason, in commercial application, the monomer of n'=1 is conventionally used. With such a monomer, there is the drawback that the ion-exchange capacity of the resultant sulfonic acid type membrane and the membrane having formed carboxylic acid groups by chemical treatment on the surface of the sulfonic acid type membrane can limitedly be increased, as disclosed by the aforesaid Japanese published unexamined patent applications. Furthermore, perhaps due to the presence of the pendant groups:

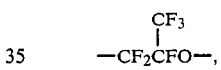

$$-CF_2CFO-,$$
$$\quad\;\; |$$
$$\quad\;\; CF_3$$

no physically tough membranes can be obtained unless the copolymerization ratio of a fluorinated olefin to the sulfur containing fluorinated vinyl ether is increased to about 6 or more. It is also expected that use of such a monomer may be one of the factors causing peel-off or cracks of the carboxylic acid layer formed when using the membrane having carboxylic acid groups and sulfonic acid groups as mentioned above under more severe conditions than conventionally used. The above drawbacks are further multiplied when the monomer of n'=2 having a larger molecular weight is used.

A copolymer of a fluorinated vinyl monomer having no ether linkage such as trifluorovinyl sulfonylfluoride with tetrafluoroethylene, as disclosed by U.S. Pat. No. 3,624,053, is deficient in fabricability into a membrane.

Japanese published unexamined patent applications No. 28588/1977, No. 23192/1977 and No. 36589/1977 disclose fluorinated cation exchange membranes prepared from copolymers of fluorinated olefins with fluorinated vinyl compounds represented by the formula:

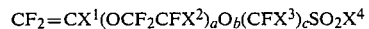

$$CF_2=CX^1(OCF_2CFX^2)_aO_b(CFX^3)_cSO_2X^4$$

wherein $X^1$ is F or $CF_3$, $X^2$ and $X^3$ are F or $C_1-C_{10}$ perfluoroalkyl, $X^4$ is F, OH, $OR^1$, OM and $NR^2R^3$($R^1$ is $C_1-C_{10}$ alkyl, $R^2$ and $R^3$ are H or one of $R^1$, and M is an alkali metal or quaternary ammonium), a is an integer of 0-3, b an integer of 0 or 1 an integer of 0-12. However, these prior publications refer to no typical example of a process for preparation of said fluorinated vinyl compounds. Nothing is taught about precursors of said compounds. Moreover, as clearly seen from the description in the specifications of said Japanese published unexamined patent applications, there is only disclosure of the compounds, copolymers and membranes derived therefrom in the Examples and preferred typical examples which are those conventionally known of the formula:

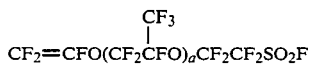

wherein a is the same as defined above, namely the group of compounds wherein c is 2, although preferred embodiments are mentioned to be those wherein $X^1=F$, $X^2=CF_3$, $X^3=F$ or $CF_3$, $X^4=F$, $a=0-1$, $b=1$ and $c=1-3$.

In the field of ion-exchange membranes, it is strongly desired to develop a membrane which exhibits high current efficiency and low electric resistance under more severe conditions, has a longer life and can be produced at low cost. The present inventors have made efforts to develop such a membrane and consequently found that the above object can be attained by use of a novel fluorinated vinyl ether compound which is derived from starting materials having specific structure. The present invention has been accomplished based on such a finding.

The first object of the present invention is to provide a fluorinated carboxylic acid or its derivative represented by the formula:

$$FSO_2(CF_2)_nY$$

wherein Y stands for $-COY^1$ or $-CN$, $Y^1$ being halogen, hydrogen, $-NH_2$, $-OM$ (M is hydrogen, a metal or ammonium group), or $-OR^3$ ($R^3$ is an alkyl having 1 to 10 carbon atoms or an aryl); and n stands for an integer of 2 to 4, and a process for producing the same.

In the prior art, as a fluorinated compound having in combination carboxylic acid derivative groups and sulfonic acid groups or groups convertible thereto in the same molecule such as said fluorinated carboxylic acid derivative, there is known only the compound $FSO_2CF_2COF$ or the compound

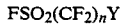

as in U.S. Pat. No. 3,301,893. There is no suggestion about a compound comprising a fluorinated alkylene group having 2 to 4 carbon atoms $-(CF_2)_n-$ between the carboxylic acid derivative groups and sulfonic acid groups or the groups convertible thereto such as the compound according to the present invention.

The fluorinated carboxylic acid or its derivative according to the present invention can be prepared by converting the compound obtained by a process comprising the following step (A), (B) or (C) according to the reaction scheme (3), (4), (5) or (6), optionally in combination with various reactions such as acid treatment, hydrolysis treatment or halogenation treatment, into a carboxylic acid derivative and sulfonic acid derivative:

(A) A method comprising the step to react tetrafluoroethylene with a carbonic acid ester having 3 to 20 carbon atoms in the presence of a mercaptide represented by the formula $R'SM^1$ ($R'$ is an alkyl having 1 to 10 carbon atoms, an aryl or a perfluoroalkyl having 1 to 10 carbon atoms; $M^1$ is an alkali metal, ammonium group or a primary to quaternary alkylammonium group):

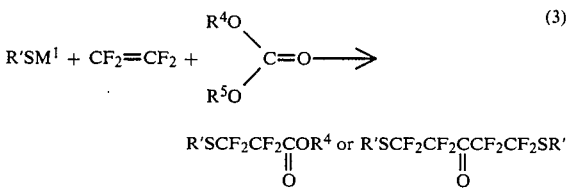

(wherein $R^4$ and $R^5$ represent alkyl or aryl, and $M^1$ is the same as defined above);

(B) A method comprising the step to react tetrafluoroethylene with a compound of the formula: $A'_2SO_2$ ($A'$ is a halogen or an alkoxy having 1 to 5 carbon atoms) in the presence of an alkali cyanide:

$$NaCN + CF_2=CF_2 + A'_2SO_2 \rightarrow NCCF_2CF_2SO_2A' \quad (4)$$

(wherein $A'$ is the same as defined above);

(C) A method comprising the step to react tetrafluoroethylene with compound of the formula: $Z'SO_2F$ or $Z'_3CSO_2F$ ($Z'$ is a halogen except for F) in the presence of a free radical initiator:

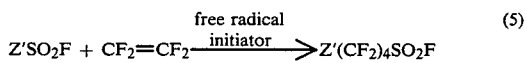

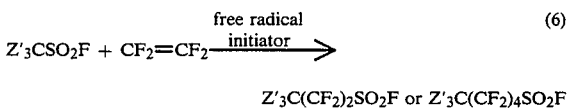

In the fluorinated carboxylic acid derivative of the present invention $FSO_2(CF_2)_nY$ (Y and n are the same as defined above), n may preferably be 2 when considering ease of preparation and the molecular weight of the fluorinated vinyl monomer prepared from said derivative. A compound wherein Y is $-COF$ is also desirable from the standpoint of usefulness as a starting material for the synthesis of a fluorinated vinyl compound. When Y is another carboxylic acid derivative, such a compound may be converted to a compound having the group $Y=-COF$.

Each of the methods (A), (B) and (C) is hereinafter described in further detail.

I. METHOD (A)

Examples of mercaptide to be used in the method (A) are derivatives of methyl mercaptan, ethyl mercaptan, propyl mercaptan, butyl mercaptan, amyl mercaptan, hexyl mercaptan, phenyl mercaptan, benzyl mercaptan, toluyl mercaptan, perfluoromethyl mercaptan, perfluoroethyl mercaptan, perfluoropropyl mercaptan, etc. in the form of sodium salts, potassium salts, cesium salts, ammonium salts, and primary to quaternary alkylammonium salts, preferably an alkyl mercaptan, especially having 1 to 5 carbon atoms, namely methyl-, ethyl-, propyl-, butyl- and amyl-mercaptan in the form of sodium salts or potassium salts.

The carbonic acid ester may be exemplified by dimethyl-, diethyl-, dipropyl-, dibutyl-, diphenyl-, or methylethyl-carbonate. Preferably, dimethyl carbonate and diethyl carbonate may be used.

The mercaptide and the carbonic acid ester are usually mixed in an inert medium. But no inert medium is necessarily required when said ester is liquid under the reaction conditions. Typical examples of a suitable inert medium are diethyl ether, tetrahydrofuran, dioxane, ethylene glycol dimethyl ether, diethylene glycol dimethyl ether, benzene and cyclohexane, having no active hydrogen and being capable of dissolving the carbonic acid ester.

The carbonic acid ester is used in an amount of 0.1 to 10 equivalents, preferably 0.5 to 5 equivalents, of the mercaptide.

Tetrafluoroethylene is usually employed in the gaseous state and may be fed into the reaction system under any desired pressure, irrespective of whether it may be pressurized, normal or reduced. Tetrafluoroethylene may be added in an amount of 0.1 to 5 equivalents, preferably 0.4 to 3 equivalents of the mercaptide.

The reaction is carried out usually at not higher than 100° C., preferably in the range from 80° to 0° C., until the pressure of tetrafluoroethylene is substantially constant under the reaction conditions employed. Formation of ketone leads to substantial decrease in the reaction yield based on the mercaptide. For this reason, it is preferred to use a lower temperature in order to suppress formation of the ketone in the reaction scheme (3). The reaction is carried out under substantially anhydrous conditions.

After completion of the reaction, the reaction system is made acidic by adding an acid. In this case, such a mineral acid as hydrochloric acid, sulfuric acid or phosphoric acid is usually used, sulfuric acid being preferred. The amount of mineral acid should be at least equivalent to the mercaptide initially employed.

In the above reaction procedure, there may also be used in place of the carbonic acid ester a N,N-dialkyl formamide having 3 to 7 carbon atoms, whereby a fluorinated aldehyde is obtained. Alternatively, in some cases, there may also be employed carbonic acid gas in place of the carbonic acid ester.

Isolation of ester, ketone or aldehyde which is the fluorinated carboxylic acid derivative may be performed by a conventional technique of separation such as phase separation, distillation or others. Said fluorinated carboxylic acid derivative of ester, ketone or aldehyde may be converted to various carboxylic acid derivatives according to suitable organic reaction procedures. For example, ester and ketone may be hydrolyzed with an alkali to give a carboxylic acid salt, which carboxylic acid salt may in turn be treated with a mineral acid to give a carboxylic acid. Further, the above carboxylic acid or salt thereof may be reacted with a chlorinating agent such as phosphorus pentachloride, thionyl chloride, etc. to obtain an acid chloride, or alternatively with sulfur tetrafluoride to obtain an acid fluoride. Also, according to the well known reaction to treat an acid chloride with sodium fluoride or potassium fluoride, an acid fluoride can be prepared. An acid fluoride is most useful from the standpoint of the starting material for synthesis of a fluorinated vinyl compound according to the reaction scheme (7) as shown below;

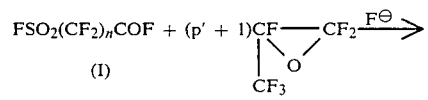

(7)

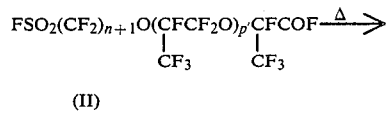

(II)

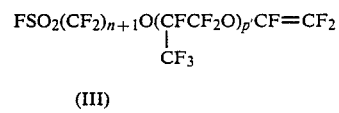

(III)

wherein n is the same as defined above, and p' is 0 or 1.

In the above fluorinated carboxylic acid derivative, the sulfide group present on the terminal end opposite to that of the carboxylic acid derivative group may also be converted to various derivatives according to suitable organic reaction procedures. For example, it may be converted by treatment with chlorine to the sulphenylchloride group or sulfonylchloride group, or by oxidation treatment to the sulfone group. Further, these groups may be subjected to hydrolysis treatment with an alkali to be converted to sulfonic acid group salts, which may be treated with phosphorus pentachloride to be converted to sulfonyl chloride groups. By treatment with sulfur tetrafluoride, such groups may also be converted to sulfonylfluoride groups. Alternatively, according to the well known reactions to treat sulfonylchloride groups with sodium fluoride or potassium fluoride, sulfonylfluoride groups can be obtained. Conversion to such various derivative groups does not interfere with the reaction according to the scheme (7), insofar as such groups have no active hydrogen.

II. METHOD (B)

The alkali metal cyanide to be used in the method (B) may include cyanides of lithium, sodium, potassium, cesium, etc. Among them, cyanides of sodium and potassium may preferably be used.

Examples of the compound of the formula $A'_2SO_2$ are sulfuryl fluoride, sulfuryl chloride, sulfuryl bromide, sulfuryl chlorofluoride, sulfuryl bromofluoride, dimethyl sulfate, diethyl sulfate, dibutyl sulfate, diamyl sulfate, and the like. In some cases, there may also be used sulfur dioxide.

The alkali metal cyanide is used usually as a dispersion in an inert medium. When the compound $A'_2SO_2$ (A' is the same as defined above) is a liquid under the reaction conditions, no such inert medium is necessarily required to be used.

As a suitable inert medium, there may be mentioned solvents having no active hydrogen such as diethyl ether, tetrahydrofuran, dioxane, ethylene glycol dimethyl ether, diethylene glycol dimethyl ether, benzene, cyclohexane, etc. Said inert medium may desirably be capable of dissolving $A'_2SO_2$.

The $A'_2SO_2$ is used in an amount of 0.1 to 10 equivalents, preferably 0.5 to 5 equivalents of the alkali metal cyanide.

Depending on the $A'_2SO_2$ employed and the properties thereof, $A'_2SO_2$ is previously charged in the reaction system to be mixed with the alkali metal cyanide, or fed into the reaction system simultaneously with tetrafluoroethylene, or fed into the reaction system previously mixed with tetrafluoroethylene.

Tetrafluoroethylene is used usually under the gaseous state and may be fed into the reaction system under any desired pressure, whether it may be pressurized, reduced or normal.

Tetrafluoroethylene is added in an amount of 0.1 to 5 equivalents, preferably 0.4 to 3 equivalents of the alkali metal cyanide.

The reaction is carried out at not higher than 250° C., preferably at not higher than 100° C., until the pressure of tetrafluoroethylene is substantially constant under the reaction conditions employed. The reaction is conducted under substantially anhydrous conditions.

Separation of fluorinated nitrile may be performed according to such procedures as phase separation or distillation. Similarly as described in the method (A), said fluorinated nitrile may be converted to various carboxylic acid derivatives or sulfonic acid derivatives, especially the sulfonylfluoride group, according to suitable organic reaction procedures, whereby it is most preferred that Y should be —COF.

III. METHOD (C)

The compound represented by the formula Z'SO$_2$F or Z'$_3$CSO$_2$F (Z' is the same as defined above) to be used in the method (C) may be exemplified by sulfuryl chlorofluoride, sulfuryl bromofluoride, trichloromethane sulfonylfluoride, tribromomethane sulfonylfluoride, and the like. Among them, sulfuryl chlorofluoride and trichloromethane sulfonylfluoride are preferred.

As the free radical initiator, there may be employed most of those conventionally used in the field of organic chemical reactions. For example, it is possible to use organic peroxides such as benzoyl peroxide, di-t-butyl peroxide, perfluoroacetyl peroxide, di-t-amyl peroxide, etc. and azo-bis type compounds such as azobisisobutyronitrile, azobisisovaleronitrile, azobisnitrile, etc.

In the present invention, instead of permitting the free radical initator to be present in the reaction, ultra-violet irradiation may be employed. Alternatively, it is also possible to effect irradiation of ultra-violet rays in the presence of a free-radical initiator.

Use of a solvent is not particularly limited, but there may be employed any solvent which is stable chemically to the free radical initiator or ultra-violet rays. Particularly, 1,1,2-trichloro-1,2,2-trifluoroethane and cyclohexane may preferably be used.

Tetrafluoroethylene is used in at least a stoichiometric amount relative to Z'SO$_2$F or Z'$_3$CSO$_2$F.

The amount of the free radical initiator used is in the range from 0.001% to 10% based on Z'SO$_2$F or Z'$_3$CSO$_2$F.

The reaction temperature may suitably be determined in view of the half-life period of the free radical initiator or other factors, usually ranging from <10° C. to 250° C., preferably from 0° C. to 150° C.

After completion of the reaction, the intermediates formed according to the reaction scheme (5) or (6) are isolated by phase separation or distillation from the reaction mixture, if desired. Said intermediates may be subjected to acid treatment using a mineral acid such as conc. sulfuric acid, sulfuric anhydride or fuming nitric acid to be converted to HOOC(CF$_2$)$_3$SO$_2$F or HOOC(CF$_2$)$_4$SO$_2$F.

The above carboxylic acid may be isolated from the reaction mixture by an isolation procedure such as extraction, phase separation or distillation. Similarly as described in the method (A), said carboxylic acid may be converted to various carboxylic acid derivatives according to suitable organic chemical reaction procedures. It is particularly preferred that Y should be —COF.

According to another preparation method, it is also possible to carry out reaction between a disulfide and tetrafluoroethylene in the presence of a free radical initiator to give an intermediate having sulfide groups at both terminal ends of the molecule, which intermediate is then subjected to chlorine treatment to provide a compound having a sulfide group at one terminal end and a sulfonyl group at the other terminal end. By treatment of said compound with hydroiodic acid, there may also prepared a compound having the sulfide group and the carboxylic acid group. By converting the sulfide group of said compound to the sulfonylfluoride group, the compound of the present invention is obtained.

Alternatively, a compound having a sulphenylchloride group and sulphenyliodide group may be allowed to react with tetrafluoroethylene in the presence of a free radical initiator, followed by treatment of the resultant intermediate with an acid such as conc. sulfuric acid, sulfuric anhydride or fuming nitric acid, to provide a compound having both a sulfide group and carboxylic acid group. By conversion of the sulfide group to a sulfonylfluoride group, the compound of the present invention is obtained.

The compound of the present invention, especially an acid fluoride, is very useful for synthesis of a fluorinated vinyl ether compound having terminal groups convertible to sulfonic acid groups as shown in the reaction scheme (7). The above compound is also useful as starting materials for production of various materials such as surfactants, fiber treatment agents, lubricants, agricultural chemicals, etc.

The fluorinated carboxylic acid derivative of the present invention can also very advantageously be produced, since no dangerous reaction is used such as the addition reaction between tetrafluoroethylene and SO$_3$ which will occur in the production of FSO$_2$CF$_2$COF and also no toxic compound such as a cyclic sultone intermediate is involved.

The second object of the present invention is to provide a novel fluorinated acid fluoride represented by the formula:

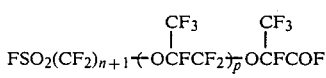

wherein n is an integer of 2 to 4, p is an integer of 0 to 50, and a process for producing said fluorinated acid fluoride compound which comprises reacting a novel compound represented by the formula:

wherein n is the same as defined above with hexafluoropropylene oxide, in the presence of a fluoride ion.

As a fluorinated compound having in combination an acid fluoride group and a functional group convertible to a sulfonic acid group in the same molecule such as said fluorinated acid fluoride compound, there is known in the prior art only a fluorinated acid fluoride of the following formula:

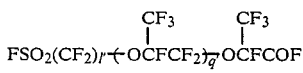

wherein $l'=2$, $q'=0-50$, as disclosed by Japanese published examined patent application No. 1664/1967. No such compound of the present invention wherein $l'$ is 3 to 5 is suggested at all in the prior art.

The fluorinated acid fluoride of the present invention can be produced according to the following reaction scheme:

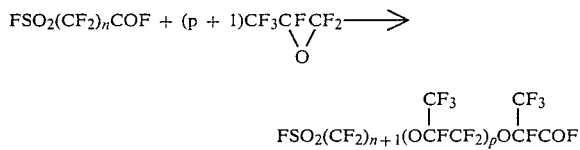

wherein n and p are the same as defined above.

The reaction between the compound of the formed $FSO_2(CF_2)_nCOF$ (wherein n is the same as defined above) and hexapropylene oxide may preferably be conducted in the presence of a fluoride ion as catalyst. This can easily be done by use of a suitable fluoride, including alkali metal fluorides such as cesium fluoride, potassium fluoride, etc.; silver fluoride; ammonium fluoride; $C_1$–$C_4$ tetraalkyl ammonium fluoride such as tetramethyl ammonium fluoride, tetraethyl ammonium fluoride and tetrabutyl ammonium fluoride; and so on.

The fluoride catalyst is usually used together with an inert liquid diluent, preferably an organic liquid, which can dissolve at least 0.001% of the fluoride selected. The fluoride catalyst may be used in an amount of about 0.01 to about 2 mole equivalent per one mole of the compound represented by the formula $FSO_2(CF_2)_nCOF$ wherein n is the same as defined above. Examples of suitable diluents are polyethers such as ethyleneglycol dimethylether, diethyleneglycol dimethylether, tetraethyleneglycol dimethylether, etc. and nitriles such as acetonitrile, propionitrile, etc. The reaction is slightly exothermic and therefore there should be provided a means for dissipating the reaction heat.

The reaction temperature may be in the range from about $-50°$ C. to about $200°$ C., preferably from about $-20°$ C. to about $150°$ C. The pressure is not a critical parameter and may either be lower than or not lower than the atmospheric pressure. The reaction time may usually be from 10 minutes to 100 hours. The applicable molar ratio of hexapropylene oxide to $FSO_2(CF_2)_nCOF$ is from about 1/20 to about 100/1. When the compound

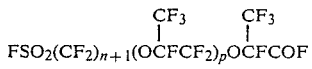

has a low p value, for example, when p is 0 or 1, the relative proportion of $FSO_2(CF_2)_nCOF$ is increased, and lower pressure and higher temperature are preferred to be selected. On the other hand, when a product with a high p value is desired to be prepared, it is preferred to increase the relative proportion of hexapropylene oxide and select higher pressure and lower temperature.

In the fluorinated acid fluoride of the present invention,

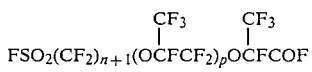

wherein n and p are the same as defined above, a compound wherein $n=2$ is preferred from the standpoint of ease of preparation.

On the other hand, a cation exchange membrane prepared from a copolymer of said fluorinated vinyl ether compound and tetrafluoroethylene may desirably have an ion-exchange capacity as large as possible. From this standpoint, said fluorinated vinyl ether compound may preferably have a molecular weight as small as possible. Accordingly, it is preferred that the value of p may be 0 or 1, most preferably 0.

The compound represented by the formula:

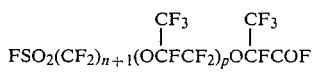

wherein n and p are the same as defined above is useful as an intermediate for the preparation of a novel fluorinated vinylether compound having functional groups convertible to sulfonic acid groups. Said compound is also useful as a starting material for surfactants, fiber treatment agents, lubricants, agricultural chemicals, etc.

The third object of the present invention is to provide a novel fluorinated vinylether compound represented by the formula:

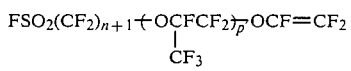

wherein n is an integer of 2 to 4 and p' is an integer of 0 to 5, and a process for preparing the same.

As a fluorinated vinylether compound having functional groups convertible to sulfonic acid groups such as said fluorinated vinylether compound, there is known in the prior art only the class of compounds:

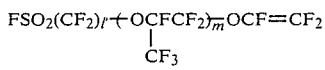

wherein $l'=2$ and $m=0$ to 2. Nothing is suggested in the prior art about the compounds of the present invention wherein $l'$ is 3 to 5.

The fluorinated vinylether compound of the present invention can be prepared according to the following reaction schemes:

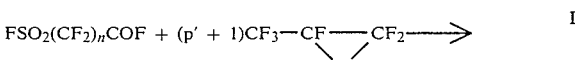
I

II

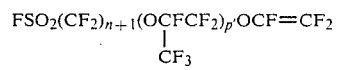

wherein n and p' are the same as defined above and W is F or OM' (M' is an alkali metal).

The fluorinated vinylether compound of the present invention represented by the formula

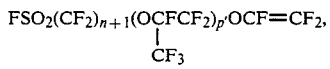

wherein n and p' are the same as defined above, can be prepared by pyrolysis of the compound of the formula:

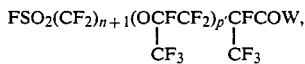

wherein n, p' and W are the same as defined above, according to the aforesaid scheme (II). In said reaction, it is preferred to use a compound wherein W=F from the standpoint of ease of use in the reaction.

Said reaction can be practiced under substantially anhydrous conditions under either pressurized, normal or reduced pressure. Usually, however, the reaction may conveniently be practiced under normal or reduced pressure.

There may also be employed a diluent to a dilution degree of 0 to 100 depending on the mode of reaction, said diluent being selected from inert gases such as nitrogen, helium, carbon dioxide, argon, etc. or inert non-protonic liquids such as polyethers.

When the terminal group is an acid fluoride group, it is possible and desirable to carry out the reaction in the presence of a metallic salt or a metal oxide. In this case, there may preferably be used a solid base, which can decompose any corrosive and toxic $COF_2$ generated, such as sodium carbonate, potassium carbonate, sodium phosphate, potassium phosphate, etc.

The reaction temperature may range from 100° to 600° C., preferably from 100° to 350° C. If the temperature is too high, side reactions such as decomposition other than vinylization are liable to occur. At too low a temperature, conversion of the starting material is lowered. The reaction time may be from 0.1 second to 10 hours, preferably from 10 seconds to 3 hours. The reaction temperature and the reaction time should suitably be selected to provide optimum conditions, for example, shorter reaction time at higher reaction temperature or longer reaction time at lower reaction temperature.

In the prior art, it has been deemed commercially difficult to prepare $FSO_2(CF_2)_2OCF=CF_2$ by a process comprising pyrolyzing

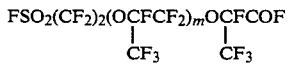

(m is an integer of 0 to 2) to form the corresponding fluorinated vinylether compound

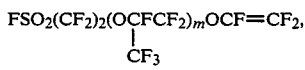

because a cyclization reaction will occur when m is 0. Moreover, depending on the conditions, cyclization may occur also during polymerization to lower the polymer properties.

In contrast, according to the present invention, use is made of the fluorinated acid fluoride represented by the formula

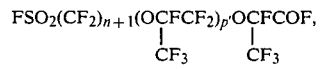

wherein n and p' are the same as defined above. Thus, due to the difference in the size of the ring, pyrolysis can be effected while causing no or only a negligible cyclization reaction. Therefore, it is possible to produce easily a fluorinated vinylether compound represented by the formula:

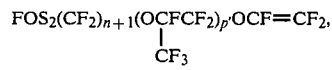

wherein n and p' are the same as defined above, even when p' may be 0. Said fluorinated vinylether compound is also free from cyclization during polymerization, thereby causing no deterioration of the properties of the resultant polymer.

In the fluorinated vinylether compound of the present invention

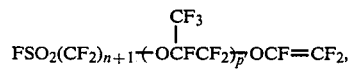

wherein n and p' are the same as defined above, it is preferred from the standpoint of ease of preparation that n is equal to.

On the other hand, the cation exchange membrane to be prepared from the copolymer of said fluorinated vinylether compound and tetrafluoroethylene is desired to have an ion-exchange capacity as large as possible. From this standpoint, said fluorinated vinylether compound may preferably be one wherein p' is equal to 0.

The fluorinated vinylether compound of the present invention can be copolymerized with, for example, tetrafluoroethylene to give a fluorinated cation exchange membrane which has the very excellent characteristic of sufficiently high ion-exchange capacity while maintaining good mechanical strength.

The fluorinated vinylether compound of the present invention may also be useful as an intermediate for synthesis of various fluorinated compounds having functional groups containing a sulfur atom at the terminal end of the molecule, for example, surfactants, fiber treating agents, lubricants, etc. It is also possible to prepare a fluorinated elastomer comprising a copolymer of the above fluorinated vinylether compound with a fluorinated olefin using said compound as a constituent or crosslinking monomer of said elastomer.

The fourth object of the present invention is to provide a novel fluorinated copolymer comprising the following recurring units (A) and (B):

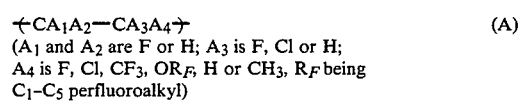

($A_1$ and $A_2$ are F or H; $A_3$ is F, Cl or H; $A_4$ is F, Cl, $CF_3$, $OR_F$, H or $CH_3$, $R_F$ being $C_1$-$C_5$ perfluoroalkyl)

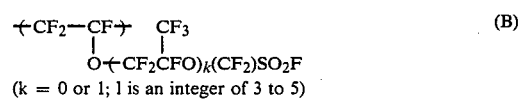

($k$ = 0 or 1; $l$ is an integer of 3 to 5)

and a process for producing the same. In the above copolymer, the molar ratio of the recurring unit (A)/(B) is desired to be in the range from 1 to 16.

When the copolymer is required particularly strongly to have resistance to heat and chemicals, as is required in preparation of a fluorinated cation exchange membrane for use in electrolysis of an aqueous alkali metal halide solution, the recurring unit (a) in the above formula may preferably be:

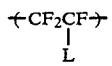

(L is F, Cl, $CF_3$, $-OR_F$ or H, $R_F$ being the same as defined above). It is particularly preferred that L should be F.

In order to produce membranes or resins having high ion-exchange capacity and physical toughness, the notation k may preferably be zero. The ratio (A)/(B) is preferred to be in the range from 1.5 to 14, more preferably from 3 to 11.

From the standpoint of ease of preparation of the monomer and the physical properties of the resultant polymer it is also preferred that l should be equal to 3.

The above copolymer is substantially a random copolymer having a molecular weight generally in the range from 8,000 to 1,000,000, having a melt index generally in the range from 0.001 g/10 min. to 500 g/10 min., as measured by use of an orifice of 2.1 mm in diameter and 8 mm in length, under a load of 2.16 kg at 250° C.

The above copolymer may conveniently be identified by measurement of the infrared absorption spectrum (IR) or attenuated total reflection (ATR) of a film of the copolymer, as shown in the Examples.

The composition of the copolymer is estimated by measurement of the ion-exchange capacity, elemental analysis or a combination thereof after converting all of the sulfur containing terminal groups to ion-exchange groups such as sulfonic acid groups or carboxylic acid groups.

The structure of the pendant groups contained in the copolymer according to the present invention can also be identified by measurement of the IR or ATR of the product formed by converting the sulfur containing terminal groups to ion-exchange groups such as sulfonic acid groups, carboxylic acid groups or sulfinic acid groups and then carrying out the reaction for elimination of said ion-exchange groups.

The fluorinated copolymer of the present invention can be prepared by copolymerization of at least one monomer selected from the group consisting of the olefins of the formula:

$$CA_1A_2=CA_3A_4$$

wherein $A_1$, $A_2$, $A_3$ and $A_4$ are the same as defined above, at least one monomer selected preferably from the group consisting of the fluorinated olefins of the formula:

$$CF_2=CFL$$

wherein L is F, Cl, $CF_3$, $-OR_F$ or H, $R_F$ being $C_1$-$C_5$ perfluoroalkyl, and at least one monomer selected from the group consisting of sulfur containing fluorinated vinylether compounds of the formula:

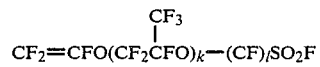

wherein k and l are the same as defined above.

In this case, there may also be copolymerized a minor amount of other vinyl compounds mixed with the above monomers. It is also possible to effect crosslinking by copolymerization of a divinyl compound such as perfluorobutadiene or perfluorodivinylether or a fluorinated vinyl compound having terminal groups capable of effecting a crosslinking reaction such as $CF_2I$, etc.

The fluorinated olefin to be used in the present invention may preferably be one containing no hydrogen atom from the standpoint of heat resistance and chemical resistance of the resultant copolymer. Above all, tetrafluoroethylene is most preferred.

Among the sulfur containing fluorinated vinylether compounds, those wherein k=0 are preferred for providing membranes with greater ion-exchange capacity and excellent physical toughness. Of course, there may also be used a minor amount of the compound wherein k=1. The class of compound wherein l=3 is also preferred from the standpoint of ease of preparation as well as the physical properties of the resultant polymer. A compound with l=6 or more can only be produced with difficultly and can provide no membrane having sufficiently high ion-exchange capacity, thus being inferior to those with l=3 to 5.

Typical example of the sulfur containing fluorinated vinylether compounds preferably used in the present invention are as follows:

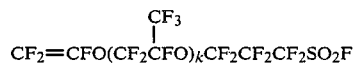

wherein k is 0 or 1, preferably 0.

As compared with the sulfur containing vinylether compound of the following formula:

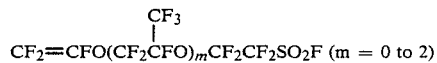

conventionally used in the prior art for preparation of fluorinated cation exchange membranes or fluorinated cation exchange resins having sulfonic acid groups and/or carboxylic acid groups, the sulfur containing fluorinated vinylether compound of the present invention is substantially free from or remarkably decreased in such cyclization reaction as previously described in the vinylization step, even when k=0, due to the difference in the number of members constituting the ring. Thus, a compound with k=0 can also easily be produced. Also during polymerization, there is no deterioration of the polymer properties due to a cyclization reaction. Accordingly, vinylether compounds with k=0 can principally be used in polymerization to provide a fluorinated copolymer containing substantially no or only a minor amount of pendant

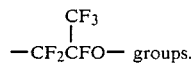 groups.

As the result, the content of fluorinated olefin can be increased at the same level as the ion-exchange capacity of the membranes or resins, whereby there can be obtained membranes or resins having higher ion-exchange capacity and also having good physical toughness.

The ratio of the olefin and the sulfur containing fluorinated vinylether compound to be copolymerized can be controlled by suitable selection of the ratio of monomers charged and the polymerization conditions.

The copolymer of the present invention may be prepared according to well known polymerization methods used for homopolymerization or copolymerization of a fluorinated ethylene. The methods for preparation of the copolymer of the present invention may include both a method in which polymerization is conducted in a non-aqueous system and a method in which polymerization is conducted in an aqueous system. The polymerization temperature may generally range from 0° to 200° C., preferably from 20° to 100° C. The pressure may be from 0° to 200 kg/cm², preferably from 1 to 50 kg/cm². The non aqueous polymerization may frequently be carried out in a fluorinated solvent. Suitable non-aqueous solvents may include inert 1,1,2-trichloro-1,2,2-trifluoroethane or perfluoro-hydrocarbons, e.g. perfluoromethylcyclohexane, perfluorodimethylcyclobutane, perfluorooctane, perfluorobenzene, etc.

As an aqueous polymerization method for preparation of the copolymer, there may be mentioned an emulsion polymerization method wherein monomers are brought into contact with an aqueous medium containing a free radical initiator and an emulsifier to provide a slurry of polymer particles or a suspension polymerization method wherein monomers are brought into contact with an aqueous medium containing both free radical initiator and dispersion stabilizer inert to telomerization to provide a dispersion of polymer particles, followed by precipitation of the dispersion. As the free radical initiator to be used in the present invention, there are redox catalysts such as ammonium persulfatesodium hydrogen sulfite, etc.; organic peroxides such as t-butyl peroxide, benzoyl peroxide, etc.; azo-bis type compounds such as azobisisobutyronitrile, and fluorine radical initiators such as $N_2F_2$, etc.

After polymerization, the polymer may be molded into membranes or granules, if desired. A conventional technique may be used for molding the polymer into a thin film or pellets by melting the polymer.

The copolymer of the present invention is useful as a starting material for preparation of a fluorinated cation exchange membrane having sulfonic acid groups and/or carboxylic acid groups. In this case, the above membrane may, sometimes preferably, be laminated with a membrane made from a copolymer having a greater copolymer ratio of the sulfur containing fluorinated vinylether compound. As the membrane to be laminated, there may be used a membrane prepared from the copolymer of the monomers selected from the group of the above sulfur containing fluorinated vinylether compounds and the groups of fluorinated olefins. Alternatively, there may also be employed a membrane prepared from the following sulfur containing fluorinated vinylether compound:

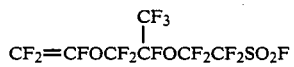

The membrane to be used for lamination may preferably have a thickness of ½ to 19/20 times the thickness of the entire laminated product in order to make the electric resistance thereof smaller.

The above membrane can be reinforced in strength by backing with a mechanical reinforcing material such as a net. As such backing materials, there may most suitably be used a net made of polytetrafluoroethylene fibers. A porous polytetrafluoroethylene sheet is also useful.

It is also possible to increase the strength of the membrane by incorporating polytetrafluoroethylene fibers during molding into a membrane. When a membrane with a laminated structure is employed, the reinforcing material may preferably be embedded on the side of the membrane with the greater copolymerization rato of sulfur containing fluorinated vinylether compound. Reinforcing materials may be embedded in the membrane by laminating, press contact embedding or vacuum fusion embedding. For example, when a net is to be embedded, a membrane is placed on a net and the surface of the membrane opposite to that contacted with the net is heated to a temperature no higher by 20° C. than the melting point of the membrane and the surface of the membrane contacted with the net maintained at a temperature higher by at least 60° C. than the melting point of the membrane, while providing a pressure difference between both sides of the membrane. The pressure on the side contacted with the net is made lower than the opposite side.

Other than the above method, it is also possible to embed the net in the membrane after converting the exchange groups on the side opposite to that contacted with the net to carboxylic acid esters.

The thickness of the membrane is generally 2500 microns or less, preferably 1000 micron or less, more preferably 500 microns or less. The lower limit is restricted by the mechanical strength required, but usually 10 microns or more.

The copolymer of the present invention may be formed into particles during polymerization or molding according to conventional procedures for preparation of ion-exchange resins, and then subjected to the reaction used for converting a membrane into a fluorinated cation exchange membrane to provide fluorinated ion-exchange resin particles.

These ion-exchange resins can be processed into any desired shape such as granules, membranes, fibers, strands, etc. By utilization of heat resistance and chemical resistance superior to hydrocarbon type resins, they are useful generally in separation processes which are based on adsorption properties such as adsorptive separation of metallic ions or separation of organic high molecular substances. They are also useful as acid catalysts for organic reactions.

The copolymer according to the present invention can also be used in the form of fibers or strands as ion-conductive reinforcing material for a fluorinated carbon exchange membrane.

Said copolymer may also be blended with other fluorocarbon type or hydrocarbon type copolymers to provide various blends useful for various purposes. It may also be provided as it is or as a mixture with a suitable solvent for use as lubricants, surfactants, etc. It is also useful as the starting material for a fluorinated elastomer.

The fluorinated copolymer of the present invention can provide a novel fluorinated cation exchange membrane or resin, comprising the following recurring units (C) and (D), by converting all of the sulfur containing terminal groups to sulfonic acid groups:

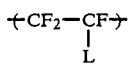
(C)

(L is F, Cl, CF₃, OR_F or H, R_F being C₁–C₅ perfluoroalkyl)

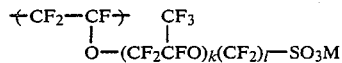
(D)

(k is 0 or 1, l is an integer of 3 to 5, and M is H, a metal or ammonium).

In the above cation exchange membrane, the relative proportion of the recurring units (C)/(D) may preferably be in the range from 1.5 to 14 more preferably from 3 to 11.

This membrane is useful as a diaphragm for use in the electrolysis of an aqueous alkali halide metal solution, electrolysis of water or fuel cells. For the reason as already mentioned, this membrane is superior to the fluorinated cation exchange membrane containing sulfonic groups conventionally used in commercial application.

The membrane of the fluorinated copolymer of the present invention can also be formed into a novel fluorinated cation exchange membrane having carboxylic acid groups and sulfonic acid groups, comprising essentially the above recurring units (C), (D) and the following recurring unit (E):

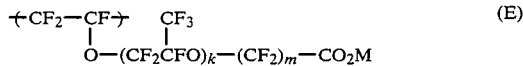
(E)

In said membrane, the ratio of the numbers of the recurring units (C), (D) and (E) may preferably be (C)/[(D)+(E)]=1.5 to 14, more preferably 3.5 to 6. When said membrane is to be used in electrolysis of an aqueous alkali metal halide solution, it is preferred that the carboxylic acid groups be distributed in the membrane locally near one surface portion of the membrane. More specifically, the carboxylic acid group density, which is defined as the percentage of the number of carboxylic acid groups based on the total number of all ion-exchange groups present in a layer substantially parallel to the surfaces of the membrane may desirably satisfy the following requirements:

(a) The carboxylic acid group density on one surface should be at least 20%; and (b) The carboxylic acid group density should gradually be decreased from said one surface toward the innerside of the membrane at the maximum gradient of 20%/micron.

One specific feature of the above membrane resides in having excellent electrolysis performance of high current efficiency and low electrolysis voltage. Another specific feature of the membrane resides in stability under more severe conditions than those usually employed, whereby said excellent electrolysis performance can be maintained for a long time. The membrane can also be produced economically with ease and at low cost.

The excellent electrolysis performance of the membrane according to the present invention may be ascribed to the specific structure of the membrane, having a carboxylic acid group density on one surface of 20% to 100%, preferably 40% or more, more preferably 60% or more, said carboxylic acid group density gradually decreasing from said one surface toward the innerside of the membrane, i.e. in the direction of thickness of the membrane. To give a quantitative expression of such a gradual decrease of carboxylic acid group density from one surface of the membrane toward the depth of the membrane in terms of the maximum gradient, which is defined as the greatest decrease of carboxylic acid group density per unit thickness in the membrane, the maximum gradient should preferably be 20 to 0.1% per one micron of the membrane thickness, more preferably 10% to 1%. As a preferable structure, said carboxylic acid group density may reach substantially zero % at a depth of not more than ½ of the entire thickness of the membrane from one surface. In other words, the carboxylic acid groups should preferably be present in the membrane locally in one half side of the membrane, being more enriched with a gradual increase the nearer to the surface on one side, while the other half side of the membrane contains other exchange groups, namely sulfonic acid groups. More preferably, the depth at which the carboxylic acid group density reaches zero % may be less than ½ of the entire thickness of the membrane, i.e. ¼ or less, most preferably 1/6 or less, to the lower limit of about 1μ.

When the above membrane is used for electrolysis of an aqueous alkali metal halide solution, it is preferred to use the membrane with the surface having higher carboxylic acid group density facing toward the cathode. With such an arrangement, said surface shrinks when contacted with a highly concentrated alkali due to the presence of carboxylic acid groups to increase the concentration of fixed ions. As the result, permeation, migration and diffusion of hydroxyl ions into the membrane can effectively be inhibited, whereby high current efficiency can be exhibited.

The carboxylic acid group density on said one surface of the membrane may be variable depending on various factors such as the value of the ratio (C)/[(D)+(E)], the current density, the temperature and the alkali concentration employed in electrolysis and can optimally be determined by controlling the conditions in preparation. Generally speaking, as the value of (C)/[(D)+(E)] is greater, the carboxylic acid group density may be lower.

On the other hand, according to a preferred embodiment of the above membrane, carboxylic acid groups are present primarily in a thin layer on the side of one surface of the membrane, only sulfonic acid groups being present in most of the residual portion. For this reason, the electric resistance in migration of alkali metal ions from the anode chamber to the cathode chamber is extremely low as compared with, for example, a membrane containing only carboxylic acid groups.

One reason why the membrane of the present invention can be used more stably than the membrane of the prior art even under more severe conditions than those conventionally used may be ascribed to the specific structure of the polymer substantially consisting of the recurring units (C), (D) and (E) as described above. For obtaining a membrane having high ion-exchange capacity as well as good physical toughness, it is preferred that the suffix k should be equal to zero, but there may also be partially mixed therewith a polymer wherein k is 1. It is also preferred from the ease of preparation of the monomer, the physical properties of the resultant polymer and greater variable range of the polymer properties that the suffix l should be equal to 3. A membrane with an l value of 6 or more is inferior to those with l values of 3 to 5 from the standpoint of difficulty in commercial production of the monomer and insufficient ion-exchange capacity obtained. A membrane wherein L is a fluorine atom is particularly preferred from the aspects of heat resistance and chemical resistance.

The specific feature of the polymer structure as mentioned above is based on the specific structure of the sulfur containing fluorinated vinylether of the following formula used for preparation of the membrane of the invention:

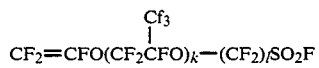

wherein k and l are the same as defined above.

The above monomer is different in the number of members of the ring in the cyclized product by-produced in the vinylization step, as compared with the sulfur containing fluorinated vinylether of the formula:

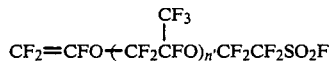

wherein n' is 0 to 2, which is used as starting material for a sulfonic acid type membrane of the prior art or a sulfonic acid type membrane having been formed by chemical treatment of carboxylic acid groups in the surface stratum thereof, and therefore it is possible to form substantially no or to decrease to a great extent the cyclization reaction in the vinylization step as mentioned above. Thus, a monomer with k=0 can easily be prepared and there is also no deterioration of polymer properties due to cyclization during polymerization.

Accordingly, since it is possible to use a monomer with k=0 as principal starting material for preparation of a membrane, the resultant polymer can have a structure containing substantially no or only a very small proportion of pendant groups:

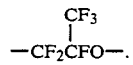

Consequently, with the same level of the ion-exchange capacity, the content of fluorinated olefin can be increased. In other words, there can be produced a physically tough membrane with enhanced ion-exchange capacity. Moreover, while its mechanism has not yet been clarified, such a membrane can maintain stable performance, being prevented from encountering problems of peel-off or crack of the carboxylic acid layer, even when used under more severe conditions than those conventionally used.

Another reason why the membrane of the present invention is stable under severe conditions may be ascribed to the relative ratio of the recurring units (C), (D) and (E), i.e. the ratio of $(C)/[(D)+(E)]$ which is generally in the range from 1.5 to 14, preferably from 3 to 11, more preferably from 3.5 to 6. When said ratio is less than 1.5, the membrane is liable to be swelled during usage and therefore cannot maintain stable performance for a long term. On the other hand, if it is greater than 14, the membrane is liable to shrink so as to make the electric resistance to the membrane impractically high.

The ion-exchange capacity of the above membrane may be represented by the following formula as being dependent on the structure of the recurring units, the ratio of recurring units and the carboxylic acid group density:

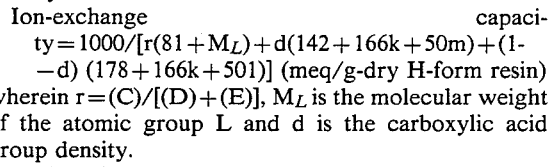

wherein $r=(C)/[(D)+(E)]$, $M_L$ is the molecular weight of the atomic group L and d is the carboxylic acid group density.

In the prior art, the ion-exchange capacity of an ion-exchange membrane has been indicated in specific numerical values, as disclosed by Japanese published unexamined patent applications No. 120492/1975, No. 130495/1976, No. 36589/1977 and No. 24176/1977, and U.S. Pat. No. 4,065,366. According to the study by the present inventors, however, the swelling and shrinking behavior of a membrane with a given species of ion-exchange groups is not controlled by the ion-exchange capacity per se of the membrane but by the most important factors including the fluorinated olefin constituting the copolymer, the copolymer ratio of the fluorinated vinylether having ion-exchange groups and the presence or absence

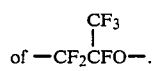

In order to obtain a membrane having sufficiently low electric resistance and good physical toughness with small swelling or shrinking characteristics when used in electrolysis, it is required to use a fluorinated vinylether having no

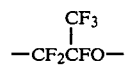

groups as principal component and to control the above copolymerization ratio within a certain range. The ion-exchange capacity as represented by the above formula is based on such considerations.

It is not clear why the above copolymerization ratio has such a decisive influence on the swelling and shrinking behavior of a membrane. For convenience of explanation, reference is made to a membrane containing the most preferred fluorinated olefin, i.e. tetrafluoroethylene. From analysis of X-ray diffraction of the membrane, tetrafluoroethylene seems to be partially crystallized. Since the degree of crystallization is greatly dependent on the above copolymerization ratio, it may be estimated that the crystallized region will function as quasi-crosslinks which control the swelling and shrinking behavior of the membrane.

In the above membrane, it is possible to provide a structure containing substantially no or a small amount of pendant groups:

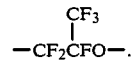

When a membrane with the same ion-exchange capacity is to be prepared, the copolymerization ratio of tetrafluoroethylene can be increased in the above membrane, as compared with a membrane prepared by use

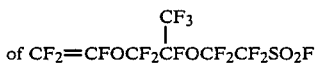
of $CF_2=CFOCF_2CFOCF_2CF_2SO_2F$ as a sulfur containing fluorinated vinylether, thereby providing a membrane having both high ion-exchange capacity and good physical toughness.

As described above, the membrane prepared from the fluorinated copolymer of the present invention is specific in having a carboxylic acid group density which is gradually decreased from the surface to the innerside, preferably at a gradient within a specific range. This is still another reason why the above membrane is by far more stable than the membrane of the prior art under more severe conditions than those conventionally used.

The membrane having a laminated structure comprising a membrane containing carboxylic acid groups and a membrane containing sulfonic acid groups, as disclosed by Japanese published unexamined patent applications No. 36589/1977 and No. 132089/1978, is incomplete in bonding as previously mentioned and liable to cause peel-off or water bubbles in a short period of time at the laminated portion.

On the other hand, according to the experience of the present inventors, even when the carboxylic acid density can be controlled to a certain extent in a membrane having carboxylic acid groups formed by chemical treatment, as disclosed by Japanese published unexamined patent applications No. 24176/1977, No. 104583/1978, No. 116287/1978 and No. 6887/1979, the resultant membrane is liable to cause peel-off or crack of the carboxylic acid layer, as compared with the membrane of the present invention, presumably due to the problem in polymeric structure as previously mentioned.

In contrast, as illustrated in the Examples, the above membrane can maintain stable performance for by far a longer time than the membranes of prior art without causing abnormal phenomena such as peel-off or crack of the carboxylic acid layer even under the conditions of a high current density of 110 A/dm² and a high temperature of 95° C. or higher.

The above membrane may also have laminated on one surface of the membrane with the lower carboxylic acid group density a fluorinated cation exchange membrane consisting substantially of the unit (C) as previously mentioned and the following recurring unit (F):

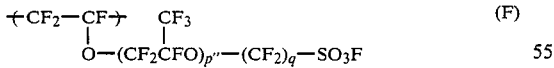
(F)

wherein $p''=0$ or 1, q is an integer of 3 to 5, and M has the same meaning as defined above, the ratio of recurring units being in the following range:

(C)/(F)<(C)/(D) or (C)/[(D)+(E)].

Such a structure is also preferred from the standpoint of lowering the electric resistance of a membrane. In this case, in order to obtain a membrane having lower electric resistance with physical toughness, it is preferred that p'' may be equal to zero and q equal to 1. It is also preferred that the thickness of the fluorinated cation exchange membrane comprising the recurring unit (F) may have a thickness ½ to 19/20 as thick as the entire membrane.

The membrane of the fluorinated copolymer of the present invention may also be formed into a fluorinated cation exchange membrane, comprising essentially the recurring units (C) and (E), having a ratio of the numbers of said recurring units of (C)/(E)=1.5 to 14, preferably 3 to 11, having substantially only carboxylic acid groups.

The above membrane having carboxylic acid groups and sulfonic acid groups can be prepared from the membrane of the fluorinated copolymer of the present invention according to the following procedures. Fluorinated cation exchange membranes having only sulfonic acid groups or carboxylic acid groups may also be prepared by utilizing a part of the reactions in said procedures.

As the first step for preparing the membrane having sulfonic acid groups and carboxylic acid groups from the membrane of the fluorinated copolymer of the present invention, a membrane prepared by the method as mentioned above comprising essentially the recurring units (C) and (B) as shown below:

(C)

(L is the same as defined above)

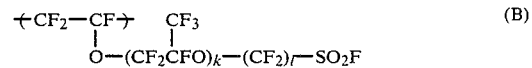
(B)

(k and l are the same as defined above) is subjected as it is, or after hydrolysis of a part or all of the membrane with an alkali, to conversion of the terminal groups to sulfonylhalide groups, preferably sulfonylchloride groups—$CF_2SO_2Cl$.

The sulfonic acid groups obtained by hydrolysis may easily be converted to sulfonylchloride groups by reaction with vapors of phosphorus pentachloride or a solution of phosphorus pentachloride dissolved in phosphorus oxychloride, an organic halide compound, etc. according to the method and the conditions as described in Japanese published unexamined patent applications No. 134888/1977 and No. 4289/1979. A mixture of phosphorus trichloride with chlorine may also be used.

Further, as the second step, a part or all of the sulfonylhalide groups, preferably sulfonylchloride groups or sulfonylfluoride groups, at the terminal end of the recurring unit (G):

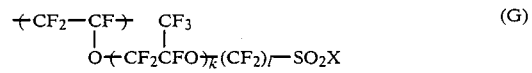
(G)

(wherein k and l are the same as defined above, X is a halogen, preferably F or Cl) are converted to carboxylic acid groups. From the standpoint of easiness in reaction and handling, sulfonylchloride groups may preferably be used.

Such a conversion can be accomplished by treatment of a membrane comprising the recurring units (C) and (G) with a reducing agent and according to the reaction method and reaction conditions as generally described in Japanese published unexamined patent applications No. 24176/1977, No. 24177/1977 and No. 132094/1978, thereby converting —$CF_2$— directly bonded to sulfur atom directly or via sulfinic acid groups into carboxylic acid groups.

The reducing agents to be used in the present invention may preferably be selected from acids having reducing ability such as hydroiodic acid, hydrobromic acid, hypophosphorous acid, hydrogen sulfide water, arsenous acid, phosphorous acid, sulfurous acid, nitrous acid, formic acid, oxalic acid, etc., their metal salts, ammonium salts, and hydrazines, from the standpoint of reactivity and ease in handling. Among them, an inorganic acid having reducing ability is most preferred. These reducing agents may be used alone or, if necessary, as a mixture.

The structure of the membrane comprising carboxylic acid groups enriched on only one surface of the membrane, which is the excellent specific feature of the above membrane may be realized easily by applying the first step reaction or preferably the second step reaction on one surface of the membrane. In case of a membrane having a laminated structure, these reactions may be applied on the surface opposite to that on which lamination is effected.

The gradient of the carboxylic acid group density may be controlled to a desired shape of the density curve by adequately controlling various factors in the reactions in the first or the second step such as temperature, time, pressure, solvent composition, etc. to thereby balance the reaction rate and the diffusion velocity of a reagent into the membrane. For ease of control, it is preferred to effect such controlling in the second step.

As a preferable method for controlling the carboxylic acid group density, there may be mentioned a method wherein the above treatment with a reducing agent is effected in the presence of at least one organic compound selected from $C_1$-$C_{12}$ alcohols, carboxylic acids, sulfonic acids, nitriles or ethers, using especially a solution of said organic compounds dissolved in an aqueous reducing agent solution. In particular, carboxylic acids may preferably be used as such organic compounds. These organic compounds may be added in an amount, which is variable depending on the membrane employed, the reducing agent and organic compound employed as well as the reaction conditions and may suitably be selected within the range of 100 ppm or more.

Examples of alcohols to be used in the present invention may include methanol, ethanol, propanol, ethylene glycol, diethylene glycol, 1,4-butane diol, 1,8-octane diol, glycerine, and the like.

As typical examples of carboxylic acids and sulfonic acids, there may be mentioned formic acid, acetic acid, propionic acid, butyric acid, iso-butyric acid, n-valeric acid, caproic acid, n-heptanoic acid, caprylic acid, lauric acid, fluoroacetic acid, chloroacetic acid, bromoacetic acid, dichloroacetic acid, malonic acid, glutaric acid, trifluoroacetic acid, perfluoropropionic acid, perfluorobutyric acid, perfluorovaleric acid, perfluorocaproic acid, perfluoro-n-heptanoic acid, perfluorocaprylic acid, perfluoroglutaric acid, trifluoromethane sulfonic acid, perfluoroheptane sulfonic acid, methane sulfonic acid, ethane sulfonic acid, propane sulfonic acid, butane sulfonic acid, pentane sulfonic acid, hexane sulfonic acid, heptane sulfonic acid, and so on. Preferably, acetic acid, propionic acid, caprylic acid, trifluoroacetic acid, perfluorocaprylic acid or perfluorobutyric acid may be used.

Typical examples of nitriles are acetonitrile, propionitrile, adiponitrile, and the like. Ethers may be exemplified by diethylether, tetrahydrofuran, dioxane, ethylene glycol dimethylether, diethylene glycol dimethyl ether, etc. Among these organic compounds, some compounds may undergo chemical changes depending on the reducing agent employed and therefore it is desired to avoid such a combination.

The gradient of the carboxylic acid group density in the membrane may be determined, as illustrated in the Examples, by staining the cross-section of a membrane with a suitable dye and observing the result of staining, or alternatively by scraping the membrane substantially in parallel to the surface thereof (usually in a thickness of about 1 to 5 micron per each scraping), subjecting the scraped face to attenuated total reflection (hereinafter referred to as ATR) and calculating from the changes in intensity of the absorption peak based on the carboxylic acid groups.

In the membrane of the present invention or other fluorinated cation exchange membranes, the pendant structure having bonded ion-exchange groups can be identified by measurement of ATR or IR absorption spectrum after the reaction for elimination of ion-exchange groups. The composition of the copolymer is estimated by a combination of ion-exchange capacity measurement and elemental analysis.

Other than the method as described above wherein a reducing agent is used, there may also be used the same method as described in Japanese published unexamined patent application No. 125986/1978, wherein sulfonyl halide groups are once converted to —$CF_2I$, followed by conversion to carboxylic acid groups. Alternatively, the membrane comprising the recurring units (B) may be irradiated with ultra-violet rays or an electron beam to be directly converted to carboxylic acid groups. It is also possible to obtain a membrane containing carboxylic acid groups with more —$CF_2$— than that obtained by use of a reducing agent according to the method as described in Japanese published unexamined patent applications No. 104583/1978 and No. 116287/1978. Said method comprises reacting a membrane having sulfonyl halide groups or a membrane having sulfinic acid groups or —$CF_2I$ obtained as intermediate in the method as described above with a compound having carbonyl groups or unsaturated bonding under the conditions to eliminate $SO_2$ or iodine atom ionically or radically. According to these methods, however, it is very difficult to control the gradient of the carboxylic acid density; many steps are required for the reaction; the cost is high; expensive reagents are necessary; side reactions can be suppressed only with difficulty; pendant groups cannot be in the form of perfluoro groups; or the membrane may be damaged physically during the treatment. In any of these respects, any of said alternative methods is inferior to the method wherein a reducing agent is used. For this reason, in preparation of a membrane to be used under more severe conditions than those conventionally used, it is more preferable to use the method employing a reducing agent than those alternative methods as mentioned above.

The third step for preparation of the membrane of the present invention is to convert all of the residual sulfur containing terminal groups to sulfonic acid groups. This can easily be done according to the reaction as mentioned in the second step reaction or by application of the reactions such as oxidation, hydrolysis, etc. as described in Japanese published unexamined patent applications No. 24176/1977 and No. 24177/1977.

As apparently seen from the preparation methods as described above, the above membrane having carboxylic acid groups and sulfonic acid groups can be derived from common starting materials according to simple reactions to have carboxylic acid groups and sulfonic acid groups. Thus, the membrane can be manufactured easily in advantageously a low cost.

The cation exchange membrane prepared from the copolymer according to the present invention may favorably be employed in electrolysis of an aqueous alkali metal halide solution. That is, the membrane is useful not only in electrolysis of an alkali metal halide under conventional electrolysis conditions, i.e. a current density of 10 to 70 A/dm², a temperature of 20° to 100° C. alkali metal halide concentration of 1 to 5N and an alkali concentration of 1 to 15N, but is also useful under severe conditions, i.e. a current density of 70 to 200 A/dm² and a temperature of 100° to 150° C., with stable performance for a long time.

The copolymer of the present invention can also be formed into granular fluorinated ion-exchange resins by forming the polymer into particles at the time of polymerization or molding according to conventional techniques for the preparation of ion-exchange resins and then applying the reactions as described above which are used in to convert the membrane of the fluorinated copolymer to the fluorinated cation exchange membrane, said resins comprising the following recurring units (A) and (D) and/or (E):

$$\text{+CA}_1\text{A}_2\text{—CA}_3\text{A}_4\text{—}) \quad (A)$$

(wherein $A_1$, $A_2$, $A_3$ and $A_4$ are the same as defined above)

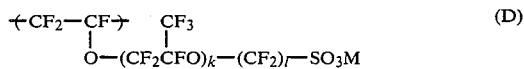

(wherein k, l and M are the same as defined above)

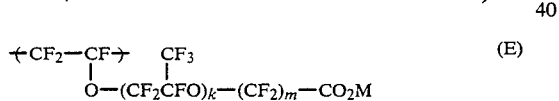

(wherein k, m and M are the same as defined above)

The present invention is illustrated in further detail by referring to the following Examples, by which the present invention is not limited.

REFERENCE EXAMPLE 1

(A) In a stainless steel autoclave of 3-liter capacity, there are charged 250 g of sodium ethyl mercaptide, 530 g of dimethyl carbonate and 750 g of tetrahydrofuran, and then the reaction system is brought into a reduced pressure of 50 to 60 mm Hg. While maintaining the temperature at 15° C. under vigorous agitation of the reaction system, tetrafluoroethylene is gradually blown into the system under reduced pressure. With the progress of the reaction, the rate of tetrafluoroethylene consumed is lowered until, finally at the tetrafluoroethylene pressure of 1 kg/cm², there is no more consumption of tetrafluoroethylene. After the reaction, the reaction mixture is neutralized with 300 g of 98% sulfuric acid. The sodium sulfate formed is filtered off and the filtrate is previously evaporated by an evaporator to remove tetrahydrofuran, followed by distillation of the residue, to obtain 520 g of the fraction of distillate at 84° C./30 mm Hg. Said fraction is found to have the structure of $C_2H_5SCF_2CF_2COOCH_3$ from elemental analysis, IR and NMR spectra.

IR characteristic absorption (liquid): 2960, 2930, 2870 cm⁻¹ ($C_2H_5$—), 1780 cm⁻¹ (—$CO_2$—), 1300–1100 cm⁻¹ (—$CF_2$—).

Elemental analysis: $C_6H_8F_4O_2S$; Calculated: C, 32.7; H, 3.6; F, 34.5; S, 14.5; Found: C, 32.2; H, 3.9; F, 33.9; S, 14.3.

(B) The compound $C_2H_5SCF_2CF_2COOCH_3$ prepared in (A) as described above (330 g) is added dropwise at room temperature over one hour, while under vigorous agitation, into a reactor wherein chlorine gas (500 ml/minute) is previously passed through trifluoroacetic acid (100 ml). After said dropwise addition, the reaction mixture is left to stand for 10 hours, followed by distillation of the product and collection of the fraction of distillate at 70°–75° C./60 mm Hg to give 310 g of said fraction of distillate.

Said fraction is identified by IR spectrum, NMR spectrum and elemental analysis, to have the formula $ClSCF_2CF_2CO_2CH_3$.

Elemental analysis values: Found: C, 21.4; H, 1.2; F, 33.1; S, 13.9; Calculated (for $C_4H_3F_4SO_2Cl$): C, 21.2; H, 1.3; F, 33.5; S, 14.1.

(C) While passing chlorine gas at the rate of 500 ml/minute into a cold water (200 ml) previously saturated with chlorine, under vigorous agitation, the sulphenylchloride prepared in (B) (226.5 g) is added gradually thereto. After the addition is completed, the reaction is continued for an additional 5 hours. Then, the lower layer is taken out to obtain 232 g of the fraction of distillate at 80°–82° C. under 60 mm Hg.

Said fraction is identified by IR spectrum, elemental analysis, and NMR spectrum to have the structure of $ClSO_2CF_2CF_2CO_2CH_3$.

IR absorption spectrum:

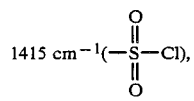

1785 cm⁻¹ (—$COOCH_3$), 2960 cm⁻¹ (—$CH_3$)

Elemental analysis: Found: C, 18.7; H, 1.0; F, 29.1; S, 12.6; Calculated (for $C_4H_3F_4SO_4Cl$): C, 18.6; H, 1.2, F, 29.4; S, 12.4.

(D) The perfluoro-3-chlorosulfonylmethyl propionate (258.5 g) obtained in (C) is neutralized with 8N-NaOH, followed by removal of water and methanol.

After the residue is dried, phosphorus pentachloride (312 g) and phosphorus oxychloride (150 g) are added thereto and the reaction is carried out under reflux on a heating bath at 130° C. for 10 hours. After the reaction, distillation of the product gives 220 g of the fraction of distillate at 70° C. under 100 mm Hg.

This substance is identified by IR absorption spectrum, elemental analysis and NMR spectrum to be $ClSO_2CF_2CF_2COCl$ (perfluoro-3-chlorosulfonylpropionyl chloride).

IR absorption spectrum: 1790 cm⁻¹ (—COCl), 1415 cm⁻¹ (—$SO_2Cl$).

Elemental analysis: Found: C, 13.4; F, 28.5; S, 12.1; Cl, 27.3 Calculated (for $C_3F_4SO_3Cl_2$): C, 13.7; F, 28.9; S, 12.2; Cl, 27.0.

EXAMPLE 1

A vessel containing sulforane (224 ml) and sodium fluoride (336 g) is heated on a heating bath at 80° C. and there is added dropwise the perfluoro-3-chlorosulfonyl-propionyl chloride (263 g) prepared in (D) of the Reference example 1. The reaction is carried out for one hour. After the reaction, the product is subjected to distillation to give 218 g of the fraction of distillate boiling at 50° to 55° C.

Said fraction is identified by IR and NMR spectra and elemental analysis to be $FSO_2CF_2CF_2COF$ (perfluoro-3-fluorosulfonyl-propionyl fluoride).

IR absorption spectrum: 1890 cm$^{-1}$ (—COF), 1470 cm$^{-1}$ (—SO$_2$F).

Elemental analysis: Found: C, 15.5; F, 49.5; S, 13.8; Calculated (for $C_3F_6SO_3$): C, 15.7; F, 50.0; S, 13.9.

EXAMPLE 2

The perfluoro-3-fluorosulfonyl-propionylfluoride (230 g) prepared in Example 1 is charged together with diethyleneglycol dimethylether (72 ml) and potassium fluoride (5.4 g) into an autoclave. While stirring the mixture at room temperature, hexafluoropropylene oxide (182.6 g) is then pressurized into the autoclave over 30 minutes and the reaction mixture is left to stand under stirring for an additional 30 minutes.

After the reaction, the reaction mixture taken out is found to be separated into two layers. The lower layer is subjected to distillation to give 225 g of a fraction boiling at 45° C. under 60 mm Hg.

Said fraction is identified by IR and NMR spectra, elemental analysis and molecular weight titration to have a structure of

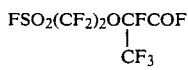

(perfluoro-6-fluorosulfonyl-3-oxa-2-methyl-hexanoyl-fluoride).

IR absorption spectrum: 1880 cm$^{-1}$ (—COF), 1465 cm$^{-1}$ (—SO$_2$F).

Elemental analysis: Found: C, 18.0; F, 57.8; S, 8.0, Calculated (for $C_6F_{12}SO_4$): C, 18.2; F, 57.6; S, 8.1.

Molecular weight titration: Titrated: 397, Calculated: 396.

EXAMPLE 3

While an electric tubular furnace previously filled with sodium carbonate (932 g) is maintained at 210° C., nitrogen is passed therethrough at the flow rate of 100 to 150 ml/minute. From the inlet of said tubular furnace, there is added dropwise 480 g of the perfluoro-6-fluorosulfonyl-3-oxa-2-methylhexanoyl fluoride prepared in Example 2 at the rate of 20 cc/hour, and the effluent is stored in a reservoir cooled with cold water. Then, the effluent is subjected to distillation to give 200 g of a fraction boiling at 64° C. under 200 mm Hg.

Said fraction is identified by IR and NMR spectra and elemental analysis to have a structure of $FSO_2(CF_2)_3OCF=CF_2$ (perfluoro-4-oxa-5-hexenesulfonyl fluoride).

IR absorption spectrum: 1840 cm$^{-1}$ (CF$_2$=CFO—), 1460 cm$^{-1}$ (—SO$_2$F)

Elemental analysis: Found: C, 18.2; F, 57.7; S, 9.5; Calculated (for $C_5F_{10}SO_3$): C, 18.2; F, 57.6; O, 14.5; S, 9.7.

COMPARATIVE EXAMPLE 1

The procedure of Example 3 is repeated except that

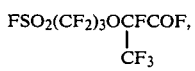

is used and passed through the sodium carbonate bed in place of

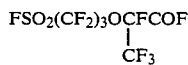

whereby no objective $CF_2=CFO(CF_2)_2SO_2F$ is obtained but only the cyclized product

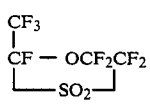

can be obtained.

EXAMPLE 4

Example 2 is repeated except that the amount of hexafluoropropylene oxide is changed to 315 g. The reaction product is subjected to distillation to give 91 g of

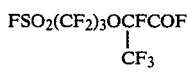

and 281 g of

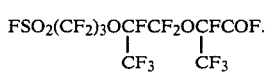

These structures are identified by IR and NMR spectra, and elemental analysis.

EXAMPLE 5

The compound

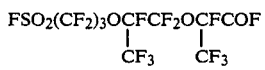

(290 g) prepared in Example 4 is introduced into a tubular furnace filled with sodium carbonate and the reaction is effected at 260° C. As the result, there is obtained 153 g of

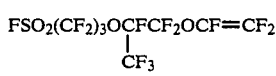

(perfluoro-4,7-dioxa-5-methyl-8-nonene sulfonylfluoride).

Said product is found to have a boiling point of 82° C./60 mm Hg and its structure is identified by IR and NMR spectra and elemental analysis.

EXAMPLE 6

An emulsion is formed by charging 10 g of $CF_2=CFO(CF_2)_3SO_2F$, 95 cc of purified water containing 1 ppm of copper sulfate, 0.28 g of ammonium persulfate and 0.90 g of ammonium perfluorooctanoate in a stainless steel autoclave of 300 cc capacity. Then, 5 cc of an aqueous 0.12% sodium hydrogen sulfite solution is added to the mixture, and polymerization is conducted under the pressure of tetrafluoroethylene of 5 kg/cm², while maintaining the temperature at 40° C. During the polymerization, the pressure of tetrafluoroethylene is controlled so as to keep constant the rate of polymerization.

The resultant polymer is found to contain 3.56 wt.% of sulfur by elemental analysis. A part of this polymer is hydrolyzed and subjected to measurement of its ion-exchange capacity. As the result, the polymer is found to have an ion-exchange capacity of 1.08 meq/g-dry resin. Thus, the ratio of the recurring units of tetrafluoroethylene and the above vinyl monomer, i.e.

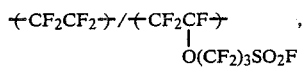

is found to be 6.0.

The above copolymer is found to have a melt index of 0.2 g/10 min., as measured under the conditions of the temperature of 275° C. and the load of 2.16 kg by means of an orifice of 2.1 mm in diameter and 8 mm in length.

The above sulfonylfluoride type copolymer is formed into a membrane with a thickness of 250μ, followed by hydrolysis with an alkali to form a sulfonic acid type membrane. Said membrane is dried and then subjected to treatment with a 1:1 mixture (weight ratio) of phosphorus pentachloride and phosphorus oxychloride at 120° C. The treated membrane is subjected to measurement of ATR, whereby the absorption by sulfonyl groups at 1470 cm$^{-1}$ observed before treatment is found to be vanished and instead thereof there appears absorption of sulfonylchloride groups at 1420 cm$^{-1}$.

One surface of said membrane having sulfonylchloride groups is treated with a mixture comprising 57% hydroiodic acid and glacial acetic acid at a volume ratio of 30:1 at 72° C. for 16 hours and then hydrolyzed with an alkali. Further, the membrane is treated with an aqueous 5% sodium hypochlorite solution at 90° C. for 16 hours. When the cross-section of the membrane is stained with an aqueous Malachite Green solution, the membrane is stained in blue to the depth of 12μ from the surface on one side, the residual portion being stained in yellow. By measurement of the ATR of the surface stained in blue, there is observed an absorption at 1690 cm$^{-1}$ due to carboxylic acid salt. The gradient of carboxylic acid group density in the layer stained in blue is measured according to the following method.

According to the method similar to that described above, there is prepared a membrane having the same exchange capacity wherein all the ion-exchange groups are converted to carboxylic acid groups. ATR of this membrane is measured and absorbance of carboxylic acid salt at 1690 cm$^{-1}$ is calculated according to the base line method, said absorbance being determined as 100. The surface layer on the side having carboxylic acid salt groups of the aforesaid membrane is scraped evenly and the scraped surface is subjected to measurement of ATR. Absorbance of carboxylic acid salt is calculated and the percentage A % based on the absorbance of the film of the above membrane containing only carboxylic acid groups is determined. On the other hand, the thicknesses before and after scraping are measured to determine the difference Bμ therebetween.

Thus, the density of carboxylic acid groups in the thickness of Bμ from the surface layer is determined as A %.

The density of carboxylic acid groups in the membrane of this Example as found in the scraped section from the surface layer is 100% and the maximum density gradient of carboxylic acid salt groups is 4.2%/μ.

The electrolysis performance of said membrane is measured according to the following method, with the surface having carboxylic acid salt groups facing toward the cathode side.

There is used an electrolytic cell comprising the anode compartment and the cathode compartment separated by said membrane with a current passage area of 0.06 dm² (2 cm×3 cm) and said membrane is assembled in the cell so that the surface having carboxylic acid groups may face toward the cathode side. As the anode, a dimensionally stable metal electrode is used and as the cathode an iron plate. Into the anode compartment is charged a saturated aqueous sodium chloride solution and the pH of the anolyte is maintained at 3 by the addition of hydrochloric acid. While 10N aqueous caustic soda solution is circulated to the cathode compartment, water is added thereto in order to maintain the concentration at a constant value.

While maintaining the temperatures in both the anode compartment and the cathode compartment at 95° C., current is passed at the current density of 110 A/dm². The current efficiency is calculated by dividing the amount of caustic soda formed in the cathode compartment by the theoretical amount calculated from the quantity of current passed.

The current efficiency and the cell voltage are measured with lapse of time to obtain the following results:

| Current passage time (hrs.): | 24 | 720 |
|---|---|---|
| Current efficiency (%): | 95 | 95 |
| Voltage (V): | 4.9 | 4.9 |

After passage of current, the membrane is observed to find no physical damage such as water bubbles, cracks or peel-off.

COMPARATIVE EXAMPLE 2

In a stainless steel autoclave of 300 cc capacity, there are charged 10 g of

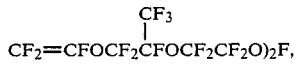

0.1 g of ammonium persulfate and water. The mixture is emulsified using ammonium perfluorooctanoate as emulsifier and polymerized at 50° C. under the pressure of tetrafluoroethylene of 3 kg/cm², while adding sodium hydrogen sulfite is co-catalyst. The ion-exchange capacity of the resultant copolymer is measured after hydrolysis of a part thereof to be 1.3 meq/g-dry resin. The ratio of the recurring units of this polymer, i.e.

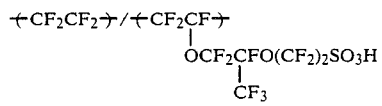

is found to be 3.3.

After washing the above polymer with water, the polymer is formed into a film with a thickness of 250µ, which is in turn hydrolyzed with an alkali. The resultant membrane is too low in mechanical strength to perform an evaluation thereof.

EXAMPLE 7

The sulfonylfluoride type polymer prepared in Example 6 is extrusion molded into a strand, which is in turn pelletized by a pelletizer to prepare granular resin with a diameter of 1 mm.

Said granular resin is treated with a solution of 3N caustic soda in 50% methanol at 60° C. for 20 hours to provide a sulfonic acid type fluorinated cation exchange resin. Said granular resin has an ion-exchange capacity, which is found to be 1.08 meq/g-dry resin, as measured by acid-base exchange.

EXAMPLE 8

The resin prepared in Example 7 is dried and then treated with a 1:1 mixture (weight ratio) of phosphorus pentachloride and phosphorus oxychloride. After said resin is washed with carbon tetrachloride and dried, it is immersed in a 1:1 mixture (volume ratio) of 57% hydroiodic acid and acetic acid to be treated at 83° C. for 100 hours therein, followed further by alkali treatment to give a carboxylic acid type fluorinated cation exchange resin. By staining with Malachite Green, the cross-section of this resin is found to be stained all over the surface. There is no sulfur detected by elemental analysis. Said resin is found to have an ion-exchange capacity of 1.19 meq/g-dry resin, as measured by acid-base exchange.

EXAMPLE 9

The resin obtained in Example 8 after washing with carbon tetrachloride and drying is treated with 57% hydroiodic acid at 72° C. for 20 hours. Then, the resin is subjected to hydrolysis treatment with 3N caustic soda/50% methanol solution, followed further by treatment at 90° C. for 16 hours with a 5% aqueous sodium hypochlorite solution to give a fluorinated cation exchange resin having both sulfonic acid groups and carboxylic acid groups. Said resin is found to have an ion-exchange capacity of 1.13 meq/g-dry resin. The cross-section of the resin is found to be stained by staining with Malachite Green such that the central portion is stained in yellow, with the circumferential portion therearound in blue.

EXAMPLE 10

An emulsion is formed by charging 10 g of

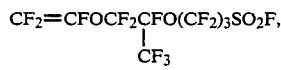

95 cc of water containing 1 ppm of copper sulfate, 0.18 g of ammonium persulfate, 2.0 g of sodium hydrogen phosphate and 1.9 g of ammonium perfluorooctanoate. Then, 5 cc of an aqueous 0.16% sodium hydrogen sulfite is added to the mixture, and copolymerization is carried out under the pressure of 4 kg/cm² of tetrafluoroethylene, while maintaining the temperature at 40° C. and controlling the pressure of tetrafluoroethylene to keep the polymerization rate constant.

The resultant polymer is found to contain 2.47% by weight of sulfur by elemental analysis. A part of the polymer is subjected to hydrolysis for measurement of ion-exchange capacity, which is found to be 0.72 meq/g-dry resin. The ratio of recurring units of tetrafluoroethylene and the vinyl monomer of the polymer, i.e.

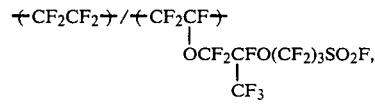

is found to be 8.9.

The above sulfonylfluoride type polymer is press molded into a membrane with a thickness of 250µ and subsequently treated similarly as described in Example 6 to prepare a cation exchange membrane having carboxylic acid groups in a surface layer on one side of the membrane. Electrolysis performance is measured similarly as in Example 6 with the surface having carboxylic acid groups facing toward the cathode side at a caustic soda concentration of 6.5N and a current density of 100 A/dm², whereby current efficiency is found to be 96%.

EXAMPLE 11

The polymer prepared in Example 6 is molded into a film with a thickness of 200µ. A fabric made of polytetrafluoroethylene fibers is embedded in this film according to the following method. The device used in this embedding procedure comprises two aluminum plates (2 cm), each being provided on the upper surface by mechanical working with a series of grooves so as to create a pressure difference across the upper surface of the plate. The pressure difference is applied through the hole bored through the side surface of the plate, which hole is connected to the grooves on the upper surface of the plate. On this plate is placed a 60-mesh wire-screen so that the pressure difference may be applied on every point on the upper surface. A sheet of asbestos paper is placed on the upper surface of the wire-screen, and on said sheet is superposed a "leno-woven" fabric with a thickness of about 0.15 mm made of polytetrafluoroethylene fibers comprising, each 25 per inch, 400 denier multi-filaments as weft and 200 denier multi-filaments×2 as warp. On said fabric is further placed the above film. The size of the film is made slightly larger than the other components and the marginals of the sheets of the fluorinated polymer are fastened onto the aluminum plates with a tape, thus forming an airtight package.

The embedding device is placed between the electrically heated hot plates, whereby the hot plate contacted with the aluminum plate is maintained at 300° C. and the hot plate contacted with the film at 185° C. for 5 minutes. Then, through the hole on the side surface of the aluminum plate, evacuation is effected to provide 100 mm Hg pressure difference. Under such conditions, the whole composite is left to stand for 3 minutes. The temperature of the hot plates is then cooled to room temperature and the pressure difference is removed. By observation of the cross-section of the film, the fabric is completely embedded within the film.

When the thus prepared membrane is treated similarly as described in Example 6, there is obtained a membrane having similar current efficiency according to the same evaluation test of electrolysis performance as described therein.

We claim:

1. A fluorinated vinyl ether compound represented by the formula:

$$FSO_2(CF_2)_{n+1}(OCFCF_2)_{p'}OCF=CF_2$$
$$\phantom{FSO_2(CF_2)_{n+1}(O}|$$
$$\phantom{FSO_2(CF_2)_{n+1}(OCFC}CF_3$$

wherein n is 2 and p' is an integer of 0 to 1.

2. A compound according to claim 1, wherein p' is 0.

* * * * *